United States Patent [19]

Lysenko et al.

[11] Patent Number: 4,562,009
[45] Date of Patent: Dec. 31, 1985

[54] HALONITRILES, THEIR PREPARATION AND USE TO MAKE HALOPYRIDINES

[75] Inventors: Zenon Lysenko; R. Garth Pews, both of Midland, Mich.

[73] Assignee: The Dow Chemical Company, Midland, Mich.

[21] Appl. No.: 555,789

[22] Filed: Nov. 28, 1983

[51] Int. Cl.[4] .................. C07C 121/34; C07C 119/02
[52] U.S. Cl. ................................ 260/465.6; 260/464; 260/465 F; 546/345
[58] Field of Search .................. 546/345; 260/465 D, 260/464, 465.6

[56] References Cited

U.S. PATENT DOCUMENTS 2,679,453  5/1954  Brett et al. .................... 546/345

OTHER PUBLICATIONS

Huff et al., Helv. Chim. Acta, 60, (1977), pp. 907–921.

Primary Examiner—Henry R. Jiles
Assistant Examiner—Robert C. Whittenbaugh

[57] ABSTRACT

Novel halonitriles, e.g., 2,4-dichloro-2-fluoro-5,5-dimethoxy-4-methylpentanenitrile, method of preparation and use to make halopyridines, some of which are novel, e.g., 2-chloro-3-fluoro-5-methylpyridine. These compounds are intermediates in the preparation of pharmaceutical and agricultural products.

8 Claims, No Drawings

HALONITRILES, THEIR PREPARATION AND USE TO MAKE HALOPYRIDINES

BACKGROUND OF THE INVENTION

This invention relates to novel nitriles, a process of producing them and their use to make novel halopyridines, pyridinols and methyl pyridines which are useful as pharmaceuticals, agricultural products and as intermediates.

The copper salt induced addition of ethyl trichloroacetate to olefins is taught by S. Naurai, N. Sonoda and S. Tsutsumi in the J. of Org. Chem., 29, 2104 (1964). The same authors describe the copper salt catalyst addition of trichloro- and dichloroacetonitriles to olefins in the J. of Org. Chem., 31, 3000-2, (1966).

The addition reaction of trichloroacetaldehyde with acrylonitrile to form 2,4,4-trichloro-4-formylbutyronitrile and its subsequent cyclization to give 2,3,5-trichloropyridine is described in U.S. Pat. No. 4,245,098.

SUMMARY OF THE INVENTION

This invention provides novel compounds having the formula

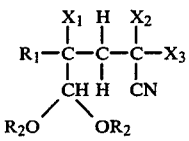

wherein $R_1$ is H, alkyl or aryl; $R_2$ is alkyl, cycloalkyl or aryl; $X_1$ is Cl, Br or I; $X_2$ is $X_1$, H, alkyl, aryl or cycloalkyl, and $X_3$ is F, Cl or Br.

The invention also provides a process for making compounds having the formula

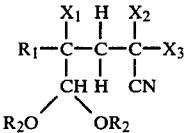

wherein $R_1$ is H, alkyl or aryl; $R_2$ is alkyl, cycloalkyl or aryl; $X_1$ is Cl, Br or I; $X_2$ is $X_1$, H, alkyl, aryl or cycloalkyl, and $X_3$ is F, Cl or Br; which comprises reacting a compound of the formula

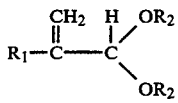

with a compound having the formula $$X_1X_2X_3CCN$$

in the presence of a catalyst in a suitable reaction medium.

In addition, this invention also provides a process for the selective reduction of halogens occupying the position next to nitrile groups by using a reducing mixture comprising, for example, a 5% cadmium amalgam in acidic acetonitrile.

In the above-described formulae, $R_1$ and $R_2$ are preferably methyl, $X_1$ is preferably Cl or Br and $X_2$ is Cl, Br or H. A most preferred class of compounds are those wherein $X_1$ is Cl, $X_3$ is F and $X_2$ is H or Cl.

The catalyst employed in the process of this invention is advantageously a transition metal catalyst, preferably a copper catalyst, and a cocatalyst such as, for example, n-tributylphosphine, triphenyl phosphine or triethylamine, is advantageously employed. The molar ratio of polyhalonitrile to olefin is advantageously from 1:1 to 1:2, and is preferably about 1:2. The reaction is advantageously carried out in an inert solvent or diluent, e.g., acetonitrile, propionitrile or butyronitrile.

The invention is further illustrated by the following examples.

EXAMPLE 1

Preparation of chlorofluoroacetonitrile

Ethyl chlorofluoroacetate (141 g, 1.1 mole) was placed in a 500 ml round bottom flask and cooled to 0° C. by means of an ice bath. A concentrated solution of ammonium hydroxide (250 ml) was added dropwise over a period of 30–45 minutes. During the course of the addition, the temperature of the reaction rose to 25° C. Upon completion of the addition, the reaction was stirred for an additional 15 minutes. Then the water and ethanol were removed in vacuo and the residue was distilled to afford 90 g of chlorofluoroacetamide (81 percent), b.p. 71°–77° C. at 1 mmHg. The chlorofluoroacetamide (90 g) obtained was then added to a 500 ml round bottom flask equipped with a distillation head and receiver and a mechanical stirrer, and containing 88 g (0.62 mole) of phosphorus pentoxide. The reaction mixture was heated until the product began to distill (160° C. pot temperature) and maintained until no further distillation occurred. The crude chlorofluoroacetonitrile was then redistilled from 1.0 g of $P_2O_5$ to afford 56 g (80 percent yield) of pure material, b.p. 66° C.

EXAMPLE 2

Preparation of bromofluoroacetonitrile

Ethyl bromofluoroacetate (50 g, 0.27 mole) was placed in a 200 ml round bottom flask and cooled to 0° C. by means of an ice bath. Ammonium hydroxide (100 ml) was added dropwise to the solution during a 20–30 minute period. During the addition, the temperature rose to 30° C. Upon completion of the addition, the reaction mixture was stirred in the ice bath until the temperature fell to 10° C. to allow the product to precipitate. The bromofluoroacetamide (35 g, 83 percent) was isolated by filtration, dried in air and used without further purification.

Bromofluoroacetamide (35 g, 0.31 mole) was taken up in 50 ml of propionitrile. Phosphorus pentoxide (25 g, 0.176 mole) was placed in a 500 ml round bottom flask equipped with a distillation head and receiver and a mechanical stirrer, and was heated to 190° C. The solution of bromofluoroacetamide was added and the product was simultaneously distilled along with propionitrile. Integration of the distillate by ¹Hnmr showed it contained 66 percent bromofluoroacetonitrile. A total of 50 ml was collected, b.p. 75°–95° C.

¹Hnmr (CDCl₃) δ 7.15 (d, 1H, C—F) $J_{HF}$ 44 Hz.
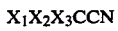

EXAMPLE 3

Preparation of dibromofluoroacetonitrile

Ethyl dibromofluoroacetate (20 g, 0.076 mole) was cooled to 0° C. by means of an ice bath in a 100 ml round bottom flask and 40 ml of concentrated NH₄OH solution was added dropwise to the stirring reaction mixture. Upon completion of the addition, the reaction mixture was stirred vigorously for 1 hour during which time the product, dibromofluoroacetamide, precipitated from solution which was isolated by filtration and air dried to afford 15.9 g in 95.6% yield.

15.9 g of dibromofluoroacetamide (0.068 mole) was mixed thoroughly with 21 g of phosphorus pentoxide and heated to 195° C. Dibromofluoroacetonitrile produced from the reaction was trapped in a dry ice acetone trap at $-78°$ C. Redistillation from a small amount of phosphorus pentoxide afforded 9.8 g (67.1% yield) of dibromofluoroacetonitrile; b.p. 83°-87° C., 760 mm/Hg.

EXAMPLE 4

Preparation of dichlorofluoroacetonitrile (a) Pentachlorofluoroacetone

A 2-liter round bottom flask equipped with a condenser and mechanical stirrer was charged with 1 liter (6.6 moles) of hexachloroacetone, 411.2 g (2.2 moles) of anhydrous antimony trifluoride and 30 ml of antimony pentachloride. The mixture was heated to 140° C. for a period of one hour then cooled to 0° C. The liquid portion of the reaction was decanted from the salts of the reaction and washed with 5×200 ml portions of 12N HCl dried over MgSO₄ and distilled. The fraction boiling at 160°-167° C. afforded 700 g of product as a 3:1 mixture of pentachlorofluoro and tetrachlorodifluoro acetones, respectively, and was used without further purification.

(b) Dichlorofluoroacetamide

The mixture (700 g) of fluoroacetones was dissolved in 700 ml of methylene chloride in a 1-liter round bottom flask. The solution was cooled to 0° C. and anhydrous ammonia gas was slowly passed into the reaction. During the course of the addition, the temperature rose to 30° C. Upon completion, the temperature dropped back down to 0° C. and the reaction mixture was stirred overnight while at room temperature. The precipitated product was isolated by filtration. The CH₂Cl₂ was removed from the filtrate and the solids were combined to give 420 g if dichlorofluoroacetamide which was used without further purification.

(c) Dichlorofluoroacetonitrile

Dichlorofluoroacetamide (200 g, 1.37 mole) was placed in a 2-liter round bottom flask, equipped with a mechanical stirrer and a distillation head and receivers. To this substrate was added 1 liter of diethylbenzene and 250 g (1.76 mole) of phosphorus pentoxide. The reaction mixture was refluxed for 2.5 hours while the product distilled overhead and was collected in a series of dry ice-acetone traps. Redistillation of the crude material from 10 g of P₂O₅ afforded 132.5 g (68.3 percent based on dichlorofluoroacetamide charged) of dichlorofluoroacetonitrile as a colorless liquid, b.p. 33°-35° C.

EXAMPLE 5

Preparation of methacrolein dimethylacetal

Methacrolein (435 ml, 5.0 moles), trimethylorthoformade (500 ml, 5.0 moles), methanol (10 ml) and p-toluenesulfonic acid (5.0 g) were placed in a 2-liter round bottom flask equipped with an efficient condenser. The reaction mixture was stirred at 5° C. After a period of 10 minutes, a vigorous refluxing took place which was self-sustaining over a 30 minute period. The reaction was allowed to stirr at room temperature overnight and then was refluxed for an additional hour. The product was obtained by fractional distillation through a 30 cm vigereaux column. The fraction boiling between 95°-106° C. was collected to afford 420 g (73 percent) of methacrolein dimethylacetal.

'Hnmr (CDCl₃): δ 1.92 (m, 3H, CH₃—$\overset{\text{O}}{\overset{\|}{\text{C}}}$); δ 3.45 (s, 6H, (OCH₃)₂); δ 4.63 (s, 1H, $\overset{|}{\text{CH}}$); δ 5.15 (m, 2H, =CH₂).

EXAMPLE 6

A solution containing 15 g (0.13 mole) of methacrolein dimethylacetal, 11 g (0.086 mole) of dichlorofluoroacetonitrile, 50 ml of propionitrile, 1.0 g CuCl and 0.4 g of triethylamine was placed in a Carius tube. The mixture was heated to 110° C. for 9 hours and then cooled. The solvent and unreacted starting materials were removed in vacuo and the residue distilled on a Kugelrohr apparatus at 130° C. and 2.5 mm Hg to afford 12.1 g of 2,4-dichloro-2-fluoro-5,5-dimethoxy-4-methyl pentanenitrile, as a mixture of diastereomers; b.p. 59°-61° C., 0.4 mm Hg; 'Hnmr (Acetone d₆ TMS) δ 1.60-1.80 (m, 3H, —CH₃); δ 2.75-3.30 (m, 2H, —CH₂—); δ 3.50-3.70

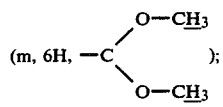

δ 4.3-4.45

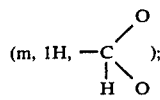

IR NaCl neat 2258 cm⁻¹; 1110 cm⁻¹; 1080 cm⁻¹.

EXAMPLE 7

A reaction mixture containing 5 g (0.045 mole) of cadmium metal dissolved in 100 g of mercury and 100 ml of acetonitrile was brought to reflux and 10.8 g (0.04 mole) of 2,4-dichloro-2-fluoro-5,5-dimethoxy-4-methyl-pentanenitrile and 0.05 mole of dimethylformamidehydrochloride in 50 ml of acetonitrile were added dropwise. After the addition was complete refluxing was maintained for an additional 5 hours. The salts and Hg were removed by filtration and the solvent was removed in vacuo. The residue was distilled through a Kuglerohr apparatus to afford 30 g of crude 4-chloro-2-fluoro-5,5-dimethoxy-4-methylpentanenitrile which was distilled through a spinning band column. Fractions boiling between 52°-55° C., 0.3 mm Hg, were collected and were shown to be essentially pure diasteromeric 4-chloro-2-fluoro-5,5-dimethoxy-4-methylpentanenitriles, 'Hnmr (Acetone d₆ TMS) δ 1.5-1.75 (m, 3H, —CH$_3$); δ 2.60 (dm, 2H, —CH$_2$—), JHF 20.76 z; δ 3.58

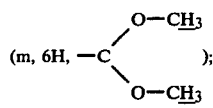

δ 4.38

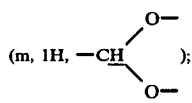

δ 5.8 (dt, 1H, —CHF—); JH$_2$F 46.6 Hz. IR NaCl neat 2260 cm$^{-1}$; 1070 cm$^{-1}$.

Analysis: Calc'd for C$_8$H$_{13}$ClFNO$_2$: C, 45.83; H, 6.25; N, 6.68. Found: C, 45.00; H, 6.22; N, 6.58.

EXAMPLE 8

Preparation of 2-fluoro-4-chloro-4-formylvaleronitrile

To a 50 ml found bottom flask was added 10.0 g (0.47 mole) of 2-fluoro-4-chloro-4-methyl-5,5-dimethyoxypentanenitrile, 15 ml of 80 percent formic acid and 5 ml of methylene chloride. The solution was heated to 70° C. for a period of 45 minutes and cooled to room temperature. Methylene chloride (150 ml) was added to the reaction mixture and said mixture was extracted with 2×50 ml portions of water and a 1×50 ml portion of saturated potassium carbonate. The organic layer was dried over MgSO$_4$ and the solvent was removed in vacuo. The residue was placed on a spinning band column and distilled to afford 5.0 g, 65.0 percent, of 2-fluoro-4-chloro-4-formylvaleronitrile, b.p. 62° C. at 0.55 mmHg as a mixture of diastereomers. 'Hnmr (acetone d$_6$): δ 1.75 (s, 3H, —CH$_3$); δ 2.50–3.10 (dm, 2H, —CH$_2$—); δ 5.80 (dm, 1H, HCF), δ 9.40–9.60 (m, 1H, CHO).

EXAMPLE 9

Preparation of 2,4-dichloro-4-methyl-5,5-dimethoxypentanenitrile

To a 100 ml round bottom flask was added 15 g of methacrolein dimethylacetal (0.13 mole), 11 g of dichloroacetonitrile (0.10 mole) and 40 ml of propionitrile with 0.5 g of CuCl and 0.5 g of tri-n-butylphosphine. The reaction was heated to reflux (97° C.) for a period of 15 hours. At this time, the reaction was cooled to room temperature. Analysis by gas chromatography showed approximately a 50–55 percent conversion of dichloroacetonitrile by area percent. The solvent and unreacted starting materials were removed in vacuo and the residue distilled on a Kugelrohr apparatus (130° C. at 3 mmHg) to afford 14.2 g of 2,4-dichloro-4-methyl-5,5-dimethoxypentanenitrile as a mixture of diastereomers, b.p. 78°–79° C., 1.10 mmHg.

'Hnmr (acetone d$_6$): δ 1.56 (s, 3H, CH$_3$); δ 2.30–2.95 (m, 2H, CH$_2$);

δ 3.45–3.65 (m, 6H, (OCH$_3$)$_2$); δ 4.40 (s, 1H, CH$\genfrac{}{}{0pt}{}{O-}{O-}$);

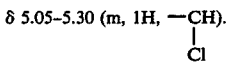

Ir (neat) NaCl 2250 cm$^{-1}$, 1450 cm$^{-1}$, 1105 cm$^{-1}$, 1080 cm$^{-1}$.

Analysis: Calc'd for C$_8$H$_{13}$Cl$_2$NO$_2$: C, 42.49; H, 5.79; N, 6.20. Found: C, 42.50; H, 5.83; N, 6.15.

EXAMPLE 10

Preparation of 2,4-dibromo-4-methyl-5,5-dimethoxypentanenitrile

To a 100 ml round bottom flask containing 40 ml of propionitrile, 1.0 g CuCl and 1.0 g of tri-n-butylphosphine were added 21.5 g (0.19 mole) of methacroleindimethylacetal and 19.0 g (0.10 mole) of dibromoacetonitrile. The mixture was heated to reflux (150° C.) for a period of 15 hours. Upon completion, the unreacted starting materials and solvent were removed in vacuo. The residue was placed on a Kugelrohr apparatus and distilled at 160° C. and 2.5 mmHg to afford diastereomeric 2,4-dibromo-4-methyl-5,5-dimethoxypentanenitrile as a deep brown oil, b.p. 99° C. at 0.5 mmHg.

'Hnmr (acetone d$_6$): δ 1.81, 1.85 (singlets, 3H, —CH$_3$);

δ 2.70–2.85 (m, 2H, CH$_2$); δ 3.60 (m, 6H, (OCH$_3$)$_2$); δ 4.45, 4.50 (singlets, 1H, —CH$\genfrac{}{}{0pt}{}{O-}{O-}$); δ 4.85–5.2 (m, 1H, BCH).

IR NaCl neat. 2255 cm$^{-1}$, 1500 cm$^{-1}$, 1075 cm$^{-1'}$, 1105 cm$^{-1}$.

Elemental Analysis Calc'd for C$_8$H$_{13}$Br$_2$NO$_2$: C, 30.50; H, 4.16; N, 4.45. Found: C, 30.60; H, 4.26; N, 4.44.

This product was also prepared by irradiating a solution of methacroleindimethylacetal (20 g) and dibromoacetonitrile (20 g) in 50 ml of propionitrile with a 275 watt sun-lamp for 14 hours. The resulting solution was stripped of light fractions in vacuo and the residue distilled on Kugelrohr at 130° C. and 1-2 mm/Hg to afford 15 g (48% isolated yield) of 2,4-dibromo-5,5-dimethoxy-4-methylpentanenitrile.

EXAMPLE 11

Preparation of 2-chloro-3-fluoro-5-methylpyridine

2-Fluoro-4-chloro-4-formylvaleronitrile, 1.92 g, was placed in a 50 ml Carius tube with 10 ml of acetonitrile. Dry HCl gas was passed into the solution for 10 seconds. The reaction mixture was then heated at 180° C. for 20 minutes. The acetonitrile was then removed under reduced pressure, dissolved in 5 ml of methylene chloride and eluted on a silica gel column (230–400 mesh, 4 cm×20 cm). The first fraction obtained contained the desired 2-chloro-3-fluoro-5-methylpyridine. Removal of the solvent in vacuo afforded 700 mg of the product (44% yield). 1 Hnmr (Acetone d$_6$); δ 2.35 (S, 3H, —CH$_3$); δ 7.50 (dd, 1H, pyr-44); δ 8.07 (broad S 14 pyr-64). IR NaCl neat. 1450 cm$^{-1}$, 1408 cm$^{-1}$, 1215 cm$^{-1}$, 1085 cm$^{-1}$, 880 cm$^{-1}$, 720 cm$^{-1}$, 711 cm$^{-1}$. Chemical Ionization Mass Spectrum (CM$_4$) MH$^+$ m/e, 146 (100%), MH$^+$ +2, m/e 148 (35%).

EXAMPLE 12

Preparation of 2,4-dibromo-2-fluoro-4-formylvaleronitrile and its conversion to 2-bromo-3-fluoro-5-methylpyridine and 2-bromo-3-fluoro-5-methylpyridine hydrobromide Dibromofluoroacetonitrile (5.0 g, 0.025 mole) and 3.5 g (0.05 mole) of methacrolein were dissolved in 50 ml of propionitrile containing 50 mg of CuCl, 50 µl of n-Bu$_3$P and 50 µl of triethylamine. This solution was placed in a Carius tube and heated at 100° C. for a period of 9 hours. Upon completion, the solvent and unreacted starting material were removed under reduced pressure. An 'Hnmr spectrum of the material showed the presence of diastereomeric 2,4-dibromo-2-fluoro-4-formylvaleronitrile along with trace amounts of 2-bromo-3-fluoro-5-methylpyridine. 'Hnmr (acetone d$_6$): δ 1.95, 2.0 (singlets, 3H, —CH$_3$); δ 3.2–3.65 (m, 24, —CH$_2$); δ 9.20, 9.35 (doublets, 1H, CHO). Distillation of this residue through a Kugelrohr apparatus at 120° C. and 3 mmHg afforded only a mixture of pyridines. The distillate which contained a precipitate was taken up in hot hexane and filtered to remove the precipitate. This precipitate was dried and purified by sublimation (50°–80° C. at 0.5 mm Hg) to afford 0.795 g (11.7 percent yield) of 2-bromo-3-fluoro-5-methylpyridine hydrobromide, m.p. 198°–203° C. (sublimed). 'Hnmr (acetone d$_6$: D$_2$O; 1:1): δ 2.45 (s, 3H, —CH$_3$); δ 7.75 (double doublet, 1H, pyr-4H); JHF 9.4 Hz; δ 8.15 (broad singlet, 1H, pyr-6H). Removal of the hexane in vacuo afforded a colorless oil which solidified on standing. Sublimation of this material (30° C. at 0.3 mm Hg) gave 0.95 g (20.0 percent yield) of 2-bromo-3-fluoro-5-methylpyridine, m.p. 32°–33° C. 'Hnmr (acetone d$_6$): δ2.35 (s, 3H, —CH$_3$); δ 7.50 (double doublet, 1H, pyr-4H), JHF 9.3 Hz; δ 8.10 (broad s, 1H, pyr-6H).

Elemental analysis Calc'd for C$_6$H$_6$Br$_2$FN: C, 26.59; H, 2.23; N, 5.17. Found: C, 26.30; H, 2.54; N, 5.29. Calc'd for C$_6$H$_5$BrFN: C, 37.92; H, 2.65; N, 7.37. Found: C, 37.24; H, 2.85; N, 6.98.

EXAMPLE 13

Preparation of 4-formyl-2,4-dichloro-2-fluorovaleronitrile

The procedure of Example 4 was repeated except to employ 11.0 grams (0.1 mole) of dichlorofluoroacetonitrile and 14.0 grams (0.2 mole) of methacrolein. The catalyst comprised 100 mg CuCl, 50 microliters of tri-n-butylphosphine and 50 microliters of triethylamine. After 9½ hours at 110° C., the unreacted starting materials and solvent were removed in vacuo and the residue distilled from a Kugelrohr apparatus (95° C. at 3.0 mm Hg) the provide 12 grams of the title product. NMR revealed the sample to be a mixture of diastereoisomers.

EXAMPLE 14

Preparation of 2,4-dichloro-2-fluoro-4-formylbutyronitrile

Employing the above general procedures a mixture of 11.0 grams (0.1 mole) of dichlorofluoroacetonitrile and 14.2 grams (0.2 mole) of acrolein in 50 ml of propionitrile containing 100 mg of CuCl and 50 microliters of triethylamine was heated to 100° C. for 9 hours, unreacted starting materials and solvent were removed in vacuo and the residue distilled from a Kugelrohr apparatus (100° C. at 5.0 mm Hg) to afford 50 grams of the titled product as a mixture of diastereomers. The yield was 27.2 percent, b.p. 43°–44° C.; 0.55 mm Hg. 'Hnmr (Acetone d$_6$) δ 1.75 (s, 3H, CH$_3$); δ 2.70–3.40 (m, 2H, —CH$_2$); δ 9.3–9.5 (m, 1H, —CHO). Ir NaCl neat 2260 cm$^1$, 1740 cm$^1$, 1450 cm$^1$, 1125 cm$^1$, 1050 cm$^1$, 910 cm$^1$. Chemical Ionization Mass Spec. (CH$_4$) MH$^+$ m/e 198 (100%); MH$^+$+2 m/e 200 (62%), m/e 226 (M+C$_2$H$_5$)$^+$, m/e 238 (M+C$_3$H$_5$)$^+$.

What is claimed is:

1. A compound having the formula

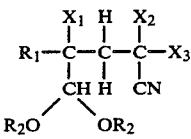

wherein R$_1$ is H or alkyl; R$_2$ is alkyl or lowercycloalkyl; X$_1$ is Cl, Br or I; X$_2$ is X$_1$, H, alkyl or cycloalkyl, and X$_3$ is F, Cl or Br.

2. Compound of claim 1 wherein R$_1$ is methyl.
3. Compound of claim 2 wherein R$_2$ is methyl.
4. Compound of claim 3 wherein X$_1$ is Cl; X$_2$ is H and X$_3$ is Cl.
5. Compound of claim 3 wherein X$_1$ is Br; X$_2$ is H and X$_3$ is Br.
6. Compound of claim 3 wherein X$_1$ and X$_2$ are Cl and X$_3$ is F.
7. Compound of claim 3 wherein X$_1$ is Cl; X$_2$ is H and X$_3$ is F.
8. Compound of claim 3 wherein X$_1$ and X$_3$ are Br and X$_2$ is H.

* * * * *

UNITED STATES PATENT AND TRADEMARK OFFICE
CERTIFICATE OF CORRECTION

PATENT NO. : 4,562,009
DATED : December 31, 1985
INVENTOR(S) : Zenon Lysenko; R. Garth Pews It is certified that error appears in the above-identified patent and that said Letters Patent is hereby corrected as shown below:   PAGE ONE OF ONE

```
Column 1, line 14, "catalyst" should read --catalyzed--.
Column 3, line 68, "made" should read --mamide--.
Column 4, line 6, "stirr" should read --stir--.
Column 5, line 24, "found" should read --round--; line 25,
"-dimethyox-" should read -- -dimethox- --.
Column 6, line 31, "(m, 2H, CH$_2$)" should read --(m, 2H, CH$_2$)--.
Column 8, line 3, "the" should read --to--.
```

Signed and Sealed this

Nineteenth Day of August 1986

[SEAL]

Attest:

DONALD J. QUIGG

Attesting Officer          Commissioner of Patents and Trademarks